US008946290B2

(12) United States Patent
Christoph

(10) Patent No.: US 8,946,290 B2
(45) Date of Patent: Feb. 3, 2015

(54) COMBINATION OF SELECTED OPIOIDS WITH MUSCARINE ANTAGONISTS FOR TREATING URINARY INCONTINENCE

(75) Inventor: Thomas Christoph, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/242,672

(22) Filed: Sep. 23, 2011

(65) Prior Publication Data

US 2012/0016023 A1 Jan. 19, 2012

Related U.S. Application Data

(63) Continuation of application No. 10/803,187, filed on Mar. 18, 2004, now abandoned, which is a continuation of application No. PCT/EP02/10460, filed on Sep. 18, 2002.

(30) Foreign Application Priority Data

Sep. 18, 2001 (DE) .................................. 101 46 275

(51) Int. Cl.
*A61K 31/216* (2006.01)
*A61K 31/137* (2006.01)
*A61K 45/06* (2006.01)

(52) U.S. Cl.
CPC ............. *A61K 31/137* (2013.01); *A61K 31/216* (2013.01); *A61K 2300/00* (2013.01); *A61K 45/06* (2013.01)
USPC ........................... 514/534; 514/649; 514/653

(58) Field of Classification Search
USPC .......................................... 514/544, 649, 653
See application file for complete search history.

(56) References Cited

U.S. PATENT DOCUMENTS

| | | | |
|---|---|---|---|
| 3,399,192 A | 8/1968 | Regnier et al. | |
| 4,442,084 A | 4/1984 | Romer | |
| 5,073,560 A | 12/1991 | Wu et al. | |
| 5,733,936 A | 3/1998 | Buschmann et al. | |
| 5,811,582 A | 9/1998 | Buschmann et al. | |
| 6,248,737 B1 | 6/2001 | Buschmann et al. | |
| 6,841,575 B2 * | 1/2005 | Christoph et al. | ............ 514/649 |
| 2002/0010178 A1 | 1/2002 | Buschmann et al. | |
| 2004/0034105 A1 | 2/2004 | Christoph et al. | |
| 2012/0016023 A1 | 1/2012 | Christoph | |

FOREIGN PATENT DOCUMENTS

| | | |
|---|---|---|
| CA | 2 386 381 A1 | 4/2001 |
| DE | 3129 982 A1 | 2/1983 |
| DE | 40 41 559 A1 | 6/1992 |
| DE | 44 26 245 A1 | 2/1996 |
| DE | 101 46 275 A1 | 4/2003 |
| GB | 857194 | 12/1960 |
| JP | 8-99939 A | 4/1996 |
| PL | 181169 B1 | 2/1996 |
| PL | 315192 A1 | 1/1997 |
| WO | WO 96/27375 A2 | 9/1996 |
| WO | WO 96/27375 A3 | 9/1996 |
| WO | WO 98/00126 A1 | 1/1998 |
| WO | WO 98/03067 A1 | 1/1998 |
| WO | WO 98/46216 A1 | 10/1998 |
| WO | WO 01/24783 A2 | 4/2001 |
| WO | WO 01/24783 A3 | 4/2001 |
| WO | WO 01/62236 A2 | 8/2001 |

OTHER PUBLICATIONS

A. Dray, et al., Inhibition of Urinary Bladder Contractions by a Spinal Action of Morphine and other Opioids., The Journal of Pharmacology and Experimental Therapeutics, Nov. 1984, pp. 254-260, vol. 231, No. 2, XP 000600400, USA.
Christopher P. Smith, et al., Genitourinary Tract Patent Update, Expert Opinion on Therapeutic Patents, 2000, pp. 17-31, 11 (1), Ashley Publications Ltd., ISSN 1354-3776, XP-002223993.
John A. Butera, et al., Recent Approaches to the Treatment of Urinary Incontinence: A Survey of Patent Activity from 1995 to 1998, Expert Opinion on Therapeutic Patents, 1998, pp. 1017-1035, 8(8), Ashley Publications Ltd., ISSN 1354-3776, XP-002223992.
K.-E. Andersson, et al., The Pharmacological Treatment of Urinary Incontinence, BJU International, 1999, pp. 923-947, 84.
J.-M. Malinovsky, MD., et al., The Urodynamic Effects of Intravenous Opioids and Ketoprofen in Humans, Anesth. Anaig., 1998, , pp. 456-461, 87, International Anesthesia Research Society.
P. T. Doyle, et al., The Effects of Drugs and Anaesthetic Agents on the Urinary Bladder and Sphincters, British Journal of Urology, 1976, pp. 329-335 48.
Isao Shimizu, et al., Effects of (+)-Pentaocine and 1,3-Di-*O*-Tolylguanidine (DTG), Sigma (δ) Ligands, on Micturition in Anaesthetized Rats., British Journal of Pharmacology, 2000, pp. 610-616, 131, Macmillan Publishers Ltd.
Alan J. Wein, Pharmacologic Options for the Overactive Bladder, Urology 51 (Supplement 2A), Feb. 1998, pp. 43-47, Elsevier Science Inc.
Yutaka Kimura, et al., Mechanisms of the Suppression of the Bladder Activity by Flavoxate, International Journal of Urology, pp. 218-227 1996, 3.
Darryl S. Chutka, et al., Urinary Incontinence in the Elderly, Drugs, Oct. 1998, pp. 587-595, 56, (4), Adis International Limited.
Hitoshi Kotani, et al., A Study of Morphine-Induced Urinary Retention in Anesthetized Rats Capable of Micturition, Japan Journal of Pharmacology, 1988, pp. 31-36, 48.

(Continued)

*Primary Examiner* — David J Blanchard
*Assistant Examiner* — Barbara Frazier
(74) *Attorney, Agent, or Firm* — Crowell & Moring LLP

(57) ABSTRACT

Active compound combinations of compounds of group A, particularly opioids such as (+)-(2R,3R)-1-dimethylamino-3-(3-methoxy-phenyl)-2-methyl-pentan-3-ol or a salt thereof with a physiologically tolerated acid, and compounds of group B, particularly anti-muscarine agents such as oxybutynin or a salt thereof with a physiologically tolerated acid suitable for treatment of an increased urge to urinate or urinary incontinence. Related pharmaceutical formulations and methods of treatment of an increased urge to urinate or urinary incontinence are also provided.

7 Claims, No Drawings

(56) References Cited

OTHER PUBLICATIONS

Benjamin Drenger, Md., et al., Urodynamic Studies After Intrathecal Fentanyl and Buprenorphine in the Dog., Anesth. Analg., 1989, pp. 348-353, 69, International Anesthesia Research Society.

Noronha-Blob et al., Enantiomers of Oxybutynin: In Vitro Pharmacological Characterization at M1, M2, and M3 Muscarinic Receptors and in Vivo Effects on Urinary Bladder Contraction, Mydriasis and Salivary Secretion in Guinea Pigs, The Journal of Pharmacology and Experimental Therapeutics, vol. 256, No. 2, pp. 562-567 (1991).

A. M. Booth et al., "Regulation of Urinary Bladder Capacity By Endogenous Opioid Peptides", The Journal of Urology, Feb. 1985, vol. 133, The Williams & Wilkins Co., (5 pages).

W. C. de Groat et al., "The Role of Neuropeptides in the Sacral Autonomic Reflex Pathways of the Cat", Journal of the Automatic Nervous System, 1983, vol. 7, Elsevier Biomedical Press, pp. 339-350.

Jackson E. Fowler et al., "Effect of Liquid Diphenoxylate Hydrochloride And Atropine Sulfate (Lomotil) Instillations on Dynamics And Function of Continent Cecal Urinary Reservoirs", The Journal of Urology, 1987, vol. 138, The Williams & Wilkes Co., (6 pages).

Christopher P Smith et al., "Genitourinary Tract Patent Update", Department of Urology, University of Pittsburgh School of Medicine, 2001, vol. 11, No. 1, Ashley Publications Ltd., pp. 17-31.

* cited by examiner

COMBINATION OF SELECTED OPIOIDS WITH MUSCARINE ANTAGONISTS FOR TREATING URINARY INCONTINENCE

CROSS REFERENCE TO RELATED APPLICATIONS

This application is a continuation co-pending application Ser. No. 10/803,187, filed Mar. 18, 2004, which in turn was a continuation of International Patent Application No. PCT/EP02/10460, filed Sep. 18, 2002, designating the United States of America, and published in German as WO 03/024444, the entire disclosure of which is incorporated herein by reference. Priority is claimed based on Federal Republic of Germany Patent Application No. DE 101 46 275.1, filed Sep. 18, 2001.

FIELD OF THE INVENTION

The invention relates to the use of a combination of compounds of group A, in particular opioids, and compounds of group B, in particular anti-muscarine agents and other substances which have a predominantly peripheral action, for the preparation of a medicament for treatment of an increased urge to urinate or urinary incontinence and to corresponding medicaments and methods for treatment of an increased urge to urinate or urinary incontinence.

BACKGROUND OF THE INVENTION

Urinary incontinence is the involuntary discharge of urine. This occurs in an uncontrolled manner when the pressure within the urinary bladder exceeds the pressure needed to close the ureter. Causes can be, on the one hand, an increased internal pressure in the bladder (e.g., due to detrusor instability) with the consequence of urgency incontinence, and, on the other, a reduced sphincter pressure (e.g., following giving birth or surgical interventions) with the consequence of stress incontinence. The detrusor is the coarsely bundled multilayered bladder wall musculature, contraction of which leads to voiding of urine, and the sphincter is the closing muscle of the urethra. Mixed forms of these types of incontinence and so-called overflow incontinence or reflex incontinence (e.g., following damage to the spinal cord) occur. Thus, for example, urinary incontinence, an urge to urinate and an increased frequency of micturition are all possible symptoms of benign prostate hyperplasia. Further details of this complex are to be found in Chutka, D. S, and Takahashi, P. Y., 1998, Drugs 560: 587-595.

The urge to urinate is the state, aimed at voiding of urine (micturition), of increased bladder muscle tension as the bladder capacity is approached (or exceeded). This tension acts here as a stimulus to micturition. An increased urge to urinate is understood here in particular as the occurrence of premature or an increased and sometimes even painful urge to urinate up to so-called strangury. This consequently leads to a significantly more frequent micturition. Causes can be, inter alia, inflammations of the urinary bladder and neurogenic bladder disorders, and also bladder tuberculosis. However, not all the causes have yet been clarified.

An increased urge to urinate and also urinary incontinence are perceived as extremely unpleasant and there is a clear need among persons affected by these indications to achieve an improvement which is as long-term as possible.

An increased urge to urinate and in particular urinary incontinence are conventionally treated with medicaments using substances which are involved in the reflexes of the lower urinary tract (Wein, A. J., 1998, Urology 51 (Suppl. 21): 43-47). These are usually medicaments which have an inhibiting action on the detrusor muscle, which is responsible for the internal pressure in the bladder. These medicaments are, e.g., parasympatholytics, such as oxybutynin, propiverine or tolterodine, tricyclic antidepressants, such as imipramine, or muscle relaxants, such as flavoxate. Other medicaments, which in particular increase the resistance of the urethra or of the neck of the bladder, show affinities for α-adrenoreceptors, such as ephedrine, for β-adrenoreceptors, such as clenbutarol, or are hormones, such as oestradiol.

The review article by K. E. Andersson et al. "The pharmacological treatment of urinary incontinence", BJU International (1999), 84, 923-947 gives an accurate insight here into the therapeutics and treatment methods used, in particular in respect of anti-muscarine agents and other substances having a peripheral action.

Certain diarylmethylpiperazines and -piperidines are also described for this indication in WO 93/15062. For tramadol also a positive effect on bladder function has been demonstrated in a rat model of rhythmic bladder contractions (Nippon-Shinyaku, WO 98/46216). There are furthermore investigations for characterization of the opioid side effect of urinary retention in the literature, from which some indications of the influencing of bladder functions by weak opioids, such as diphenoxylate (Fowler et al., 1987 J. Urol 138:735-738) and meperidine (Doyle and Briscoe, 1976 Br J Urol 48:329-335), by mixed opioid agonists/antagonists, such as buprenorphine (Malinovsky et al., 1998 Anesth Analg 87:456-461; Drenger and Magora, 1989 Anesth Analg 69:348-353), pentazocine (Shimizu et al. (2000) Br. J. Pharmacol. 131 (3): 610-616) and nalbuphine (Malinovsky et al., 1998, loc. cit.), and by potent opioids, such as morphine ((Malinovsky et al., 1998 loc. cit.; Kontani and Kawabata, (1988); Jpn J. Pharmacol. September; 48(1):31) and fentanyl (Malinovsky et al., 1998 loc. cit.) result. Nevertheless, these investigations were usually carried out in analgesically active concentrations.

In the case of the indications in question here, it should be remembered that it is in general a matter of very long-term uses of medicaments and, in contrast to many situations where analgesics are employed, those affected are faced with a situation which is very unpleasant but not intolerable. It is therefore to be ensured here—even more so than with analgesics—that side effects are avoided if the person affected does not want to exchange one evil for another. Also, analgesic actions are also largely undesirable during permanent treatment of urinary incontinence.

SUMMARY OF THE INVENTION

The object of the present invention was therefore to provide substances or substance combinations which are helpful for treatment of an increased urge to urinate or urinary incontinence and, at the active doses, preferably at the same time show fewer side effects and/or analgesic actions than known from the prior art, in particular show a synergistic effect for treatment of urinary incontinence.

It has now been found, surprisingly, that a combination of compounds of group A, the opioids and other substances which have a central action and can interact with opioid receptors and the effects of which can be antagonized by naloxone, or in particular substances which act via an opiate receptor, in particular the μ-receptor, and compounds of group B, which comprises muscarine antagonists and other substances which are known to be active in urinary incontinence and have a predominantly peripheral action, have an outstanding action on bladder function. These combinations furthermore proved to be so active at very low doses—significantly beyond that expected—that it was possible to employ the combined active compounds in a low dose. As a result, in therapeutic use the side effects which otherwise occur at the higher dosages necessary decrease significantly, while the therapeutic action is retained in full by this combination of peripheral anti-muscarine effect acting predominantly directly on the bladder or bladder musculature and central opioid effect or μ-receptor effect.

The invention accordingly provides the use of an active compound combination of at least one of the compounds A and at least one of the compounds B, with compound A chosen from:

Group a) comprising: tramadol, O-demethyltramadol, or O-demethyl-N-mono-demethyl-tramadol, optionally in the form of their racemates, their isolated or pure stereoisomers, in particular enantiomers or diastereomers, or in the form of mixtures of the stereoisomers, in particular the enantiomers or diastereomers, in any desired mixing ratio; in the form of their acids or their bases or in the form of their salts, in particular the physiologically acceptable salts, or in the form of their solvates, in particular the hydrates;

Group b) comprising:
codeine
dextropropxyphene
dihydrocodeine
diphenoxylate
ethylmorphine
meptazinol
nalbuphine
pethidine (meperidine)
tilidine
tramadol
viminol
butorphanol
dextromoramide
dezocine
diacetylmorphine (heroin)
hydrocodone
hydromorphone
ketobemidone
levomethadone
levomethadyl acetate (1-α-acetylmethadol (LAAM))
levorphanol
morphine
nalorphine
oxycodone
pentazocine
piritramide
alfentanil
buprenorphine
etorphine
fentanyl
remifentanil
sufentanil optionally in the form of their racemates, their isolated stereoisomers, in particular enantiomers or diastereomers, or in the form of mixtures of the stereoisomers, in particular the enantiomers or diastereomers, in any desired mixing ratio; in the form of their acids or their bases or in the form of their salts, in particular the physiologically acceptable salts, or in the form of their solvates, in particular the hydrates;

Group c) comprising:
1-phenyl-3-dimethylamino-propane compounds according to the general formula I

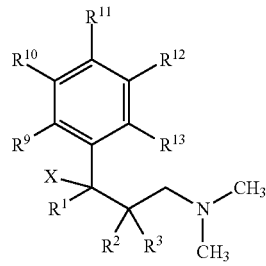

wherein

X is chosen from OH, F, Cl, H or $OC(O)R^7$, where $R^7$ is chosen from $C_{1-3}$-alkyl, branched or unbranched, saturated or unsaturated, unsubstituted or mono- or polysubstituted, $R^1$ is chosen from $C_{1-4}$-alkyl, branched or unbranched, saturated or unsaturated, unsubstituted or mono- or polysubstituted, $R^2$ and $R^3$ in each case independently of one another are chosen from H or $C_{1-4}$-alkyl, branched or unbranched, saturated or unsaturated, unsubstituted or mono- or polysubstituted, or $R^2$ and $R^3$ together form a saturated $C_{4-7}$-cycloalkyl radical, unsubstituted or mono- or polysubstituted, $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$ CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, $CO(OC_{1-5}$-alkyl), CONH—$C_6H_4$—($C_{1-3}$-alkyl), $CO(C_{1-5}$-alkyl), CO—$CHR^{17}$—$NHR^{18}$, CO—$C_{1-6}H_4$—$R^{15}$, where $R^{15}$ is ortho-$OCOC_{1-3}$-alkyl or meta- or para-$CH_2N(R^{16})_2$ where $R^{18}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and R18 in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, $OCH=CH$, $CH=CHO$, $CH=C(CH3)O$, $OC(CH3)=CH$, $(CH_2)_4$ or $OCH=CHO$ ring, optionally in the form of their racemates, their isolated stereoisomers, in particular enantiomers or diastereomers, or in the form of mixtures of the stereoisomers, in particular the enantiomers or diastereomers, in any desired mixing ratio; in the form shown or in the form of their acids or their bases or in the form of their salts, in particular the physiologically acceptable salts, or in the form of their solvates, in particular the hydrates;

Group d) comprising:
substituted 6-dimethylaminomethyl-1-phenylcyclohexane compounds according to the general formula II

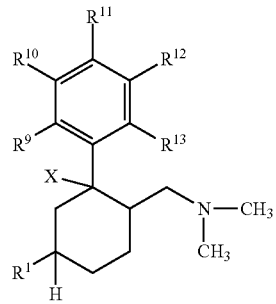

wherein
X is chosen from OH, F, Cl, H or OC(O)$R^7$, where $R^7$ is chosen from $C_{1-3}$-alkyl, branched or unbranched, saturated or unsaturated, unsubstituted or mono- or polysubstituted, $R^1$ is chosen from $C_{1-4}$-alkyl, benzyl, $CF_3$, OH, $OCH_2$—$C_6H_5$, O—$C_{1-4}$-alkyl, Cl or F and $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, CO—$C_6H_4$—$R^{15}$, where $R^{15}$ is ortho-OCO$C_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and R18 in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, optionally in the form of their racemates, their isolated stereoisomers, in particular enantiomers or diastereomers, or in the form of mixtures of the stereoisomers, in particular the enantiomers or diastereomers, in any desired mixing ratio; in the form shown or in the form of their acids or their bases or in the form of their salts, in particular the physiologically acceptable salts, or in the form of their solvates, in particular the hydrates;
and/or Group e) comprising:
6-dimethylaminomethyl-1-phenyl-cyclohexane compounds according to the general formula III

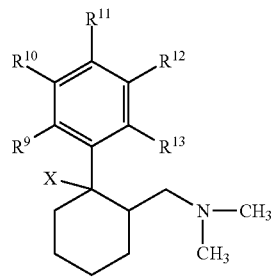

wherein
X is chosen from OH, F, Cl, H or OC(O)$R^7$, where $R^7$ is chosen from $C_{1-3}$-alkyl, branched or unbranched, saturated or unsaturated, unsubstituted or mono- or polysubstituted, and $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, CO—$C_6H_4$—$R^{15}$, where $R^{15}$ is ortho-OCO$C_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and R18 in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted,
or $R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, with the proviso that if $R^9$, $R^{11}$ and $R^{13}$ correspond to H and one of $R^{10}$ or $R^{12}$ corresponds to H and the other corresponds to $OCH_3$, X may not be OH, optionally in the form of their racemates, their isolated stereoisomers, in particular enantiomers or diastereomers, or in the form of mixtures of the stereoisomers, in particular the enantiomers or diastereomers, in any desired mixing ratio; in the form shown or in the form of their acids or their bases or in the form of their salts, in particular the physiologically acceptable salts, or in the form of their solvates, in particular the hydrates;

and with at least one of the compounds B chosen from:
the anti-muscarine agents: atropine, oxybutinin, propiverine, propantheline, emepronium, trospium, tolterodine, darifenacin and α,α-diphenylacetic acid 4-(N-methylpiperidyl) ester, as well as duloxetine, imipramine and desmopressin, optionally in the form of their racemates, their isolated stereoisomers, in particular enantiomers or diastereomers, or in the form of mixtures of the stereoisomers, in particular the enantiomers or diastereomers, in any desired mixing ratio; in the form of their acids or their bases or in the form of their salts, in particular the physiologically acceptable salts, or in the form of their solvates, in particular the hydrates;

for the preparation of medicament for treatment of an increased urge to urinate or urinary incontinence.

Surprisingly, it has been found that the combination of the substances mentioned has a significantly positive influence on certain physiological parameters, which are of importance in cases of an increased urge to urinate or urinary incontinence. Each individual of these compounds can mean a significant alleviation in the symptomatic picture of the patient affected.

In the context of this invention, alkyl or cycloalkyl radicals are understood as meaning saturated and unsaturated (but not aromatic), branched, unbranched and cyclic hydrocarbons, which can be unsubstituted or mono- or polysubstituted. In this context, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4- or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents, C1-, C2-, C3-, C4-, C5-, C6-, C7-, C8-, C9-, C10-, C11-, C12-, C13-, C14-, C15-, C16-, C17- or C18-alkyl. Furthermore, $C_{3-4}$-cycloalkyl represents C3- or C4-cycloalkyl, C5-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. In respect of cycloalkyl, the term also includes saturated cycloalkyls in which one or 2 carbon atoms are replaced by a heteroatom, S, N or O. However, the term cycloalkyl also includes, in particular, mono- or poly-, preferably monounsaturated cycloalkyls without a heteroatom in the ring as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl, $CHF_2$, $CF_3$ or $CH_2OH$, as well as pyrazolinone, oxopyrazolinone, [1,4]dioxane or dioxolane.

In connection with alkyl and cycloalkyl—as long as this is not expressly defined otherwise—the term substituted here in the context of this invention is understood as substitution of at least one (optionally also several) hydrogen radical(s) by F, Cl, Br, I, $NH_2$, SH or OH, where "polysubstituted" or "substituted" in the case of polysubstitution is to be understood as meaning that the substitution takes place both on different and on the same atoms several times with the same or different substituents, for example three times on the same C atom as in the case of $CF_3$, or at different places as in the case of —CH(OH)—CH=CH—$CHCl_2$. Particularly preferred substituents here are F, Cl and OH. In respect of cycloalkyl, the hydrogen radical can also be replaced by $OC_{1-3}$-alkyl or $C_{1-3}$-alkyl (in each case mono- or polysubstituted or unsubstituted), in particular methyl, ethyl, n-propyl, i-propyl, $CF_3$, methoxy or ethoxy.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$— etc.

An aryl radical is understood as meaning ring systems with at least one aromatic ring, but without heteroatoms in even only one of the rings. Examples are phenyl, naphthyl, fluoranthenyl, fluorenyl, tetralinyl or indanyl, in particular 9H-fluorenyl or anthracenyl radicals, which can be unsubstituted or mono- or polysubstituted.

A heteroaryl radical is understood as meaning heterocyclic ring systems with at least one unsaturated ring, which contain one or more heteroatoms from the group consisting of nitrogen, oxygen and/or sulfur and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo-1,2,5thiadiazole, benzothiazole, indole, benzotriazole, benzodioxolane, benzodioxane, carbazole, indole and quinazoline.

In this context, in connection with aryl and heteroaryl, substituted is understood as meaning substitution of the aryl or heteroaryl by $R^{23}$, $OR^{23}$ a halogen, preferably F and/or Cl, a $CF_3$, a CN, an $NO_2$, an $NR^{24}R^{25}$, a $C_{1-6}$-alkyl (saturated), a $C_{1-6}$-alkoxy, a $C_{3-8}$-cycloalkoxy, a $C_{3-8}$-cycloalkyl or a $C_{2-6}$-alkylene.

In this context, the radical $R^{23}$ represents H, a $C_{1-10}$-alkyl, preferably a $C_{1-6}$-alkyl, an aryl or heteroaryl or an aryl or heteroaryl radical bonded via a $C_{1-3}$-alkylene group, where these aryl and heteroaryl radicals may not themselves be substituted by aryl or heteroaryl radicals. The radicals $R^{24}$ and $R^{25}$ are identical or different and denote H, a $C_{1-10}$-alkyl, preferably a $C_{1-6}$-alkyl, an aryl, a heteroaryl or an aryl or heteroaryl radical bonded via a $C_{1-3}$-alkylene group, where these aryl and heteroaryl radicals may not themselves be substituted by aryl or heteroaryl radicals. Alternatively, the radicals $R^{24}$ and $R^{25}$ together denote $CH_2CH_2OCH_2CH_2$, $CH_2CH_2NR^{26}CH_2CH_2$ or $(CH_2)_{3-6}$, and the radical $R^{26}$ denotes H, a $C_{1-10}$-alkyl, preferably a $C_{1-6}$-alkyl, an aryl or heteroaryl radical or an aryl or heteroaryl radical bonded via a $C_{1-3}$-alkylene group, where these aryl and heteroaryl radicals may not themselves be substituted by aryl or heteroaryl radicals.

The term salt in the context of this invention is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes which are complex via ionic interactions.

The term physiologically acceptable salt (in particular with cations or bases) in the context of this invention is understood as meaning salts of at least one of the compounds according to the invention—usually a (deprotonated) acid—as the anion with at least one preferably inorganic cation, which are physiologically acceptable—in particular when used on humans and/or mammals. Particularly preferred salts are those of the alkali metals and alkaline earth metals, but also with $NH_4^+$, but in particular (mono-) or (di-)sodium, (mono-) or (di-)potassium, magnesium or calcium salts.

The term physiologically acceptable salt (in particular with anions or acids) in the context of this invention is furthermore understood as meaning salts of at least one of the compounds according to the invention—usually protonated, for example on the nitrogen—as the cation with at least one anion, which are physiologically acceptable—in particular when used on humans and/or mammals. In particular, in the context of this invention this is understood as meaning the salt formed with a physiologically acceptable acid, namely salts of the particular active compound with inorganic or organic acids which are physiologically acceptable—in particular when used on humans and/or mammals. Examples of physiologically acceptable salts of particular acids are salts of hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, a-liponic acid, acetylglycine, acetylsalicylic acid, hippuric acid and/or aspartic acid. The hydrochloride salt is particularly preferred.

Suitable salts in the context of this invention and in each use described and each of the medicaments described are salts of the particular active compound with inorganic or organic acids and/or a sugar substitute, such as saccharin, cyclamate or acesulfam. However, the hydrochloride is particularly preferred.

Compounds of group c) and their preparation are known from DE 44 26 245 A1 and U.S. Pat. No. 6,248,737. Compounds of group d) and e) and their preparation are known from DE 195 25 137 A1 and U.S. Pat. No. 5,733,936 and US RE37355E.

In a preferred embodiment, for the use according to the invention the compound A in group a) is chosen from:
tramadol, (+)-tramadol, (+)—O-demethyltramadol or (+)—O-demethyl-N-mono-demethyl-tramadol,
preferably tramadol or (+)-tramadol,
in particular (+)-tramadol.

In a preferred embodiment, for the use according to the invention the compound A in group b) is chosen from:
codeine
dextropropxyphene
dihydrocodeine
diphenoxylate
ethylmorphine
meptazinol
nalbuphine
pethidine (meperidine)
tilidine
viminol
butorphanol
dezocine
nalorphine
pentazocine
buprenorphine
preferably
codeine
dextropropxyphene
dihydrocodeine
meptazinol
nalbuphine
tilidine
buprenorphine In a preferred embodiment, for the use according to the invention the compound A in group c) is chosen from compounds according to formula I for which:
X is chosen from
OH, F, Cl, OC(O)CH$_3$ or H, preferably OH, F, OC(O)CH$_3$ or H,
and/or
R$^1$ is chosen from
C$_{1-4}$-alkyl, saturated and unsubstituted, branched or unbranched; preferably CH$_3$, C$_2$H$_5$, C$_4$H$_9$ or t-butyl, in particular CH$_3$ or C$_2$H$_5$, and/or
R$^2$ and R$^3$ independently of one another are chosen from
H, C$_{1-4}$-alkyl, saturated and unsubstituted, branched or unbranched; preferably H, CH$_3$, C$_2$H$_5$, i-propyl or t-butyl, in particular H or CH$_3$, preferably R$^3$=H,
or
R$^2$ and R$^3$ together form a C$_{5-6}$-cycloalkyl radical, saturated or unsaturated, unsubstituted or mono- or polysubstituted, preferably saturated and unsubstituted, in particular cyclohexyl.
and/or
R$^9$ to R$^{13}$, where 3 or 4 of the radicals R$^9$ to R$^{13}$ must correspond to H, independently of one another are chosen from
H, Cl, F, OH, CF$_2$H, CF$_3$ or C$_{1-4}$-alkyl, saturated and unsubstituted, branched or unbranched; OR$^{14}$ or SR$^{14}$, where R$^{14}$ is chosen from C$_{1-3}$-alkyl, saturated and unsubstituted, branched or unbranched;
preferably H, Cl, F, OH, CF$_2$H, CF$_3$, OCH$_3$ or SCH$_3$ or R$^{12}$ and R$^{11}$ form a 3,4-OCH=CH ring
in particular
if R$^9$, R$^{11}$ and R$^{13}$ correspond to H, one of R$^{10}$ or R$^{12}$ also corresponds to H while the other is chosen from:
Cl, F, OH, CF$_2$H, CF$_3$, OR$^{14}$ or SR$^{14}$, preferably OH, CF$_2$H, OCH$_3$ or SCH$_3$
or
if R$^9$ and R$^{13}$ correspond to H and R$^{11}$ corresponds to OH, OCH$_3$, Cl or F, preferably Cl, one of R$^{10}$ or R$^{12}$ also corresponds to H while the other corresponds to OH, OCH$_3$, Cl or F, preferably Cl,
or
if R$^9$, R$^{10}$, R$^{12}$ and R$^{13}$ correspond to H, R$^{11}$ is chosen from CF$_3$, CF$_2$H, Cl or F, preferably F,
or
if R$^{10}$, R$^{11}$ and R$^{12}$ correspond to H, one of R$^9$ or R$^{13}$ also corresponds to H while the other is chosen from OH, OC$_2$H$_5$ or OC$_3$H$_7$.

In this context, it is particularly preferable for compounds of group c) if compounds of the formula I where R$^3$=H are in the form of the diastereomers with the relative configuration Ia

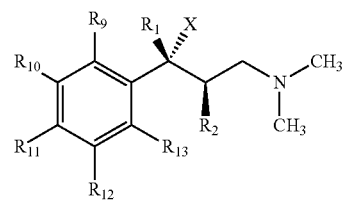

Ia in particular are used in mixtures with a higher content of this diastereomer compared with the other diastereomer or as the isolated diastereomer and/or
the compounds of the formula I are used in the form of the (+)-enantiomer, in particular in mixtures with a higher content of the (+)-enantiomer compared with the (−)-enantiomer of a racemic compound or as the isolated (+)-enantiomer.

In this context, it is particularly preferable if compound A chosen from the following group is used:
(2RS,3RS)-1-dimethylamino-3-(3-methoxy-phenyl)-2-methyl-pentan-3-ol
(2R,3R)-1-dimethylamino-3-(3-methoxy-phenyl)-2-methyl-pentan-3-ol,
(+)-(2R,3R)-1-dimethylamino-3-(3-methoxy-phenyl)-2-methyl-pentan-3-ol,
(2RS,3RS)-3-(3,4-dichlorophenyl)-1-dimethylamino-2-methyl-pentan-3-ol,
(2RS,3RS)-3-(3-difluoromethyl-phenyl)-1-dimethylamino-2-methyl-pentan-3-ol,
(2RS,3RS)-1-dimethylamino-2-methyl-3-(3-methylsulfanyl-phenyl)-pentan-3-ol,
(3RS)-1-dimethylamino-3-(3-methoxy-phenyl)-4,4-dimethyl-pentan-3-ol,
(2RS,3RS)-3-(3-dimethylamino-1-ethyl-1-hydroxy-2-methyl-propyl)-phenol,
(1RS,2RS)-3-(3-dimethylamino-1-hydroxy-1,2-dimethyl-propyl)-phenol,
(+)-(1R,2R)-3-(3-dimethylamino-1-hydroxy-1,2-dimethyl-propyl)-phenol,
(+)-(1R,2R)-3-(3-dimethylamino-1-hydroxy-1,2-dimethyl-propyl)-phenol,
(1R,2R)-3-(3-dimethylamino-1-ethyl-2-methyl-propyl)-phenol,
(−)-(1R,2R)-3-(3-dimethylamino-1-ethyl-2-methyl-propyl)-phenol,
(1S,2S)-3-(3-dimethylamino-1-ethyl-2-methyl-propyl)-phenol,
(+)-(1S,2S)-3-(3-dimethylamino-1-ethyl-2-methyl-propyl)-phenol,
(+)-(1R,2R)-acetic acid 3-dimethylamino-1-ethyl-1-(3-methoxy-phenyl)-2-methyl-propyl ester,
(1RS)-1-(1-dimethylaminomethyl-cyclohexyl)-1-(3-methoxy-phenyl)-propan-1-ol,
(2RS,3RS)-3-(4-chlorophenyl)-1-dimethylamino-2-methyl-pentan-3-ol,
(+)-(2R,3R)-3-(3-dimethylamino-1-ethyl-1-hydroxy-2-methyl-propyl)-phenol,
(2RS,3RS)-4-dimethylamino-2-(3-methoxy-phenyl)-3-methyl-butan-2-ol and
(+)-(2R,3R)-4-dimethylamino-2-(3-methoxy-phenyl)-3-methyl-butan-2-ol,
preferably as the hydrochloride.

In a preferred embodiment, for the use according to the invention the compound A in group d) is chosen from compounds according to formula II for which:
X is chosen from
OH, F, Cl, OC(O)CH$_3$ or H, preferably OH, F or H, in particular OH,
and/or
R$^1$ is chosen from
C$_{1-4}$-alkyl, CF$_3$, OH, O—C$_{1-4}$-alkyl, Cl or F, preferably OH, CF$_3$ or CH$_3$,
and/or
R$^9$ to R$^{13}$, where 3 or 4 of the radicals R$^9$ to R$^{13}$ must correspond to H, independently of one another are chosen from
H, Cl, F, OH, CF$_2$H, CF$_3$ or C$_{1-4}$-alkyl, saturated and unsubstituted, branched or unbranched; OR$^{14}$ or SR$^{14}$, where R$^{14}$ is chosen from C$_{1-3}$-alkyl, saturated and unsubstituted, branched or unbranched;
preferably H, Cl, F, OH, CF$_2$H, CF$_3$, OCH$_3$ or SCH$_3$ $_{or\,R}$$^{12}$ and R$^{11}$ form a 3,4-OCH=CH ring
in particular
if R$^9$, R$^{11}$ and R$^{13}$ correspond to H, one of R$^{10}$ or R$^{12}$ also corresponds to H while the other is chosen from:
Cl, F, OH, CF$_2$H, CF$_3$, OR$^{14}$ or SR$^{14}$, preferably OH, CF$_2$H, OR$^{14}$ or SCH$_3$, in particular OH or OC$_{1-3}$-alkyl, preferably OH or OCH$_3$,
or
if R$^9$ and R$^{13}$ correspond to H and R$^{11}$ corresponds to OH, OCH$_3$, Cl or F, preferably Cl, one of R$^{10}$ or R$^{12}$ also corresponds to H while the other corresponds to OH, OCH$_3$, Cl or F, preferably Cl,
or
if R$^9$, R$^{10}$, R$^{12}$ and R$^{13}$ correspond to H, R$^{11}$ is chosen from CF$_3$, CF$_2$H, Cl or F, preferably F,
or
if R$^{10}$, R$^{11}$ and R$^{12}$ correspond to H, one of R$^9$ or R$^{13}$ also corresponds to H while the other is chosen from OH, OC$_2$H$_5$ or OC$_3$H$_7$.
very particularly preferably
if R$^9$, R$^{11}$ and R$^{13}$ correspond to H, one of R$^{10}$ or R$^{12}$ also corresponds to H while the other is chosen from:
Cl, F, OH, SH, CF$_2$H, CF$_3$, OR$^{14}$ or SR$^{14}$, preferably OH or OR$^{14}$, in particular OH or OC$_{1-3}$-alkyl, preferably OH or OCH$_3$.

In this context, it is particularly preferable for compounds of group d) if compounds of the formula II are in the form of the diastereomers with the relative configuration IIa

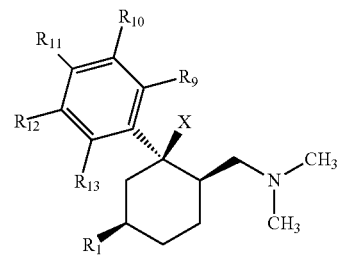

IIa in particular are used in mixtures with a higher content of this diastereomer compared with the other diastereomer or as the isolated diastereomer,
and/or
the compounds of the formula II are used in the form of the (+)-enantiomer, in particular in mixtures with a higher content of the (+)-enantiomer compared with the (−)-enantiomer of a racemic compound or as the isolated (+)-enantiomer.

In this context, it is particularly preferable if compound A chosen from the following group is used:
(1RS, 3RS, 6RS)-6-dimethylaminomethyl-1-(3-methoxy-phenyl)-cyclohexane-1,3-diol,
(+)-(1R,3R,6R)-6-dimethylaminomethyl-1-(3-methoxy-phenyl)-cyclohexane-1,3-diol,
(1RS, 3RS, 6RS)-6-dimethylaminomethyl-1-(3-hydroxy-phenyl)-cyclohexane-1,3-diol,
(1RS, 3SR, 6RS)-6-dimethylaminomethyl-1-(3-methoxy-phenyl)-cyclohexane-1,3-diol,
(+)-(1R,2R,5S)-3-(2-dimethylaminomethyl-1-hydroxy-5-methyl-cyclohexyl)-phenol or (1RS,2RS, 5RS)-3-(2-dimethylaminomethyl-1-hydroxy-5-trifluoromethyl-cyclohexyl)-phenol,
preferably as the hydrochloride.

In a preferred embodiment, for the use according to the invention the compound A in group e) is chosen from compounds according to formula III for which:

X is chosen from
  OH, F, Cl, OC(O)CH$_3$ or H, preferably OH, F or H, in particular F or H,
and/or
$R^9$ to $R^{13}$, where 3 or 4 of the radicals $R^9$ to $R^{13}$ must correspond to H, independently of one another are chosen from
  H, Cl, F, OH, CF$_2$H, CF$_3$ or C$_{1-4}$-alkyl, saturated and unsubstituted, branched or unbranched; OR$^{14}$ or SR$^{14}$, where R$^{14}$ is chosen from C$_{1-3}$-alkyl, saturated and unsubstituted, branched or unbranched;
  preferably H, Cl, F, OH, CF$_2$H, CF$_3$, OCH$_3$ or SCH$_3$
or $R^{12}$ and $R^{11}$ form a 3,4-OCH=CH ring
in particular characterized in that
  if $R^9$, $R^{11}$ and $R^{13}$ correspond to H, one of $R^{10}$ or $R^{12}$ also corresponds to H while the other is chosen from:
    Cl, F, OH, CF$_2$H, CF$_3$, OR$^{14}$ or SR$^{14}$, preferably OH, CF$_2$H, OR$^{14}$ or SCH$_3$, in particular OH or OC$_{1-3}$-alkyl, preferably OH or OCH$_3$,
  or
  if $R^9$ and $R^{13}$ correspond to H and $R^{11}$ corresponds to OH, OCH$_3$, Cl or F, preferably Cl, one of $R^{10}$ or $R^{12}$ also corresponds to H while the other corresponds to OH, OCH$_3$, Cl or F, preferably Cl,
  or
  if $R^9$, $R^{10}$, $R^{12}$ and $R^{13}$ correspond to H, $R^{11}$ is chosen from CF$_3$, CF$_2$H, Cl or F, preferably F,
  or
  if $R^{10}$, $R^{11}$ and $R^{12}$ correspond to H, one of $R^9$ or $R^{13}$ also corresponds to H while the other is chosen from OH, OC$_2$H$_5$ or OC$_3$H$_7$,
  very particularly preferably
  if $R^9$, $R^{11}$ and $R^{13}$ correspond to H, one of $R^{10}$ or $R^{12}$ also corresponds to H while the other is chosen from:
    Cl, F, OH, SH, CF$_2$H, CF$_3$, OR$^{14}$ or SR$^{14}$, preferably OH or OR$^{14}$, in particular OH or OC$_{1-3}$-alkyl, preferably OH or OCH$_3$.

In this context, it is particularly preferable for compounds of group e) if compounds of the formula III are in the form of their diastereomers with the relative configuration IIIa

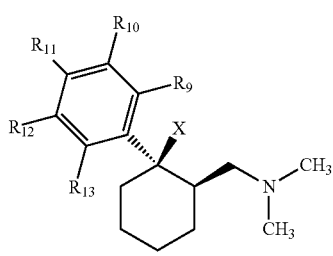

IIIa in particular are used in mixtures with a higher content of this diastereomer compared with the other diastereomer or as the isolated diastereomer
and/or
the compounds of the formula III are used in the form of the (+)-enantiomer, in particular in mixtures with a higher content of the (+)-enantiomer compared with the (−)-enantiomer of a racemic compound or as the isolated (+)-enantiomer.

In this context, it is particularly preferable if compound A chosen from the following group is used:
  (+)-(1R,2R)-3-(2-dimethylaminomethyl-1-fluoro-cyclohexyl)-phenol,
  (+)-(1S,2S)-3-(2-dimethylaminomethyl-cyclohexyl)-phenol or
  (1S,2S)-3-(2-dimethylaminomethyl-cyclohexyl)-phenol or
  (−)-(1R,2R)-3-(2-dimethylamino methyl-cyclohexyl)-phenol,
  (1R,2R)-3-(2-dimethylaminomethyl-cyclo hexyl)-phenol,
  (−)-(1R,2R)-[2-(3-methoxy-phenyl)-cyclohexylmethyl]-dimethylamine,
  (1R,2R)-[2-(3-methoxy-phenyl)-cyclohexylmethyl]-dimethylamine,
preferably as the hydrochloride.

For a particularly preferred use, compound B is chosen from:
  darifenacin, duloxetine, oxybutinin or tolterodine,
  preferably is chosen from
  duloxetine, oxybutinin or tolterodine,
  preferably is chosen from
  oxybutinin or tolterodine.

Although the uses according to the invention show only a low degree of side effects, it may also be of advantage, for example to avoid certain forms of dependency, also to use morphine antagonists, in particular naloxone, naltrexone and/or levallorphan, in addition to the combination of compounds A and B.

The invention also provides an active compound combination of at least one of the compounds A and at least one of the compounds B, with compound A chosen from:
  Group a) comprising:
    tramadol, O-demethyltramadol or O-demethyl-N-monodemethyl-tramadol, optionally in the form of their racemates, their isolated stereoisomers, in particular enantiomers or diastereomers, or in the form of mixtures of the stereoisomers, in particular the enantiomers or diastereomers, in any desired mixing ratio; in the form of their acids or their bases or in the form of their salts, in particular the physiologically acceptable salts, or in the form of their solvates, in particular the hydrates;
  Group b) comprising:
    codeine
    dextropropxyphene
    dihydrocodeine
    diphenoxylate
    ethylmorphine
    meptazinol
    nalbuphine
    pethidine (meperidine)
    tilidine
    tramadol
    viminol
    butorphanol
    dextromoramide
    dezocine
    diacetylmorphine (heroin)
    hydrocodone
    hydromorphone
    ketobemidone
    levomethadone
    levomethadyl-acetate (1-α-acetylmethadol (LAAM))
    levorphanol morphine
nalorphine
oxycodone
pentazocine
piritramide
alfentanil
buprenorphine
etorphine
fentanyl
remifentanil
sufentanil optionally in the form of their racemates, their isolated stereoisomers, in particular enantiomers or diastereomers, or in the form of mixtures of the stereoisomers, in particular the enantiomers or diastereomers, in any desired mixing ratio; in the form of their acids or their bases or in the form of their salts, in particular the physiologically acceptable salts, or in the form of their solvates, in particular the hydrates;

Group c) comprising:

1-phenyl-3-dimethylamino-propane compounds according to the general formula I

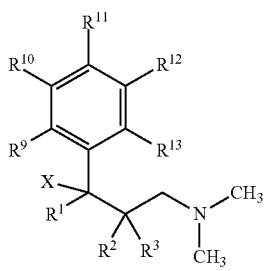

I wherein

X is chosen from OH, F, Cl, H or OC(O)$R^7$, where $R^7$ is chosen from $C_{1-3}$-alkyl, branched or unbranched, saturated or unsaturated, unsubstituted or mono- or polysubstituted, $R^1$ is chosen from $C_{1-4}$-alkyl, branched or unbranched, saturated or unsaturated, unsubstituted or mono- or polysubstituted, $R^2$ and $R^3$ in each case independently of one another are chosen from H or $C_{1-4}$-alkyl, branched or unbranched, saturated or unsaturated, unsubstituted or mono- or polysubstituted, or $R^2$ and $R^3$ together form a saturated $C_{4-7}$-cycloalkyl radical, unsubstituted or mono- or polysubstituted, $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, CO—$C_6H_4$—$R^{15}$, where $R^{15}$ is ortho-OCO$C_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and $R^{18}$ in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, optionally in the form of their racemates, their isolated stereoisomers, in particular enantiomers or diastereomers, or in the form of mixtures of the stereoisomers, in particular the enantiomers or diastereomers, in any desired mixing ratio; in the form shown or in the form of their acids or their bases or in the form of their salts, in particular the physiologically acceptable salts, or in the form of their solvates, in particular the hydrates;

Group d) comprising:

substituted 6-dimethylaminomethyl-1-phenylcyclohexane compounds according to the general formula II

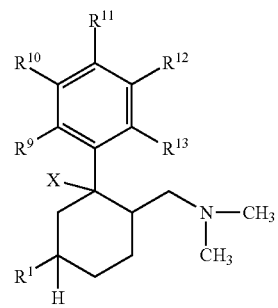

II wherein

X is chosen from OH, F, Cl, H or OC(O)$R^7$, where $R^7$ is chosen from $C_{1-3}$-alkyl, branched or unbranched, saturated or unsaturated, unsubstituted or mono- or polysubstituted, $R^1$ is chosen from $C_{1-4}$-alkyl, benzyl, $CF_3$, OH, $OCH_2$—$C_6H_5$, O—$C_{1-4}$-alkyl, Cl or F and $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, CO(O$C_{1-5}$-alkyl), CONH—$C_6H_4$—($C_{1-3}$-alkyl), CO($C_{1-5}$-alkyl), CO—$CHR^{17}$—$NHR^{18}$, CO—$C_6H_4$—$R^{15}$, where $R^{15}$ is ortho-OCO$C_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated, unsubstituted or mono- or polysubstituted;

where $R^{17}$ and R18 in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, optionally in the form of their racemates, their isolated stereoisomers, in particular enantiomers or diastereomers, or in the form of mixtures of the stereoisomers, in particular the enantiomers or diastereomers, in any desired mixing ratio; in the form shown or in the form of their acids or their bases or in the form of their salts, in particular the physiologically acceptable salts, or in the form of their solvates, in particular the hydrates;

and/or

Group e) comprising:

6-dimethylaminomethyl-1-phenyl-cyclohexane compounds according to the general formula III wherein X is chosen from OH, F, Cl, H or $OC(O)R^7$, where $R^7$ is chosen from $C_{1-3}$-alkyl, branched or unbranched, saturated or unsaturated, unsubstituted or mono- or polysubstituted, and $R^9$ to $R^{13}$ in each case independently of one another are chosen from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$; $SO_2CH_3$, $SO_2CF_3$, CN, $COOR^{14}$, $NO_2$, $CONR^{17}R^{18}$; $C_{1-6}$-alkyl, branched or unbranched, saturated or unsaturated, unsubstituted or mono- or polysubstituted; phenyl, unsubstituted or mono- or polysubstituted;

where $R^{14}$ is chosen from $C_{1-6}$-alkyl; pyridyl, thienyl, thiazolyl, phenyl, benzyl or phenethyl, in each case unsubstituted or mono- or polysubstituted; PO(O—$C_{1-4}$-alkyl)$_2$, $CO(OC_{1-5}$-alkyl), CONH—$C_6H_4$—($C_{1-3}$-alkyl), $CO(C_{1-5}$-alkyl), CO—$CHR^{17}$—$NHR^{18}$, CO—$C_6H_4$—$R^{15}$, where $R^{15}$ is ortho-$OCOC_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups can be branched or unbranched, saturated or unsaturated or mono- or polysubstituted;

where $R^{17}$ and $R^{18}$ in each case independently of one another are chosen from H; $C_{1-6}$-alkyl, branched or unbranched, saturated or unsaturated, unsubstituted or mono- or polysubstituted; phenyl, benzyl or phenethyl, in each case unsubstituted or mono- or polysubstituted, or $R^9$ and $R^{10}$ or $R^{10}$ and $R^{11}$ together form an $OCH_2O$, $OCH_2CH_2O$, OCH=CH, CH=CHO, CH=C(CH3)O, OC(CH3)=CH, $(CH_2)_4$ or OCH=CHO ring, with the proviso that if $R^9$, $R^{11}$ and $R^{13}$ correspond to H and one of $R^{10}$ or $R^{12}$ corresponds to H and the other corresponds to $OCH_3$, X may not be OH, optionally in the form of their racemates, their isolated stereoisomers, in particular enantiomers or diastereomers, or in the form of mixtures of the stereoisomers, in particular the enantiomers or diastereomers, in any desired mixing ratio; in the form shown or in the form of their acids or their bases or in the form of their salts, in particular the physiologically acceptable salts, or in the form of their solvates, in particular the hydrates;

and with at least one of the compounds B chosen from:

the anti-muscarine agents: atropine, oxybutinin, propiverine, propantheline, emepronium, trospium, tolterodine, darifenacin and α,α-diphenylacetic acid 4-(N-methylpiperidyl) ester, as well as duloxetine, imipramine and desmopressin, optionally in the form of their racemates, their isolated stereoisomers, in particular enantiomers or diastereomers, or in the form of mixtures of the stereoisomers, in particular the enantiomers or diastereomers, in any desired mixing ratio; in the form of their acids or their bases or in the form of their salts, in particular the physiologically acceptable salts, or in the form of their solvates, in particular the hydrates.

For the active compound combination, it is particularly preferable if the compound A in group a) is chosen from:
tramadol, (+)-tramadol, (+)—O-demethyltramadol or (+)—O-demethyl-N-mono-demethyl-tramadol,
preferably tramadol or (+)-tramadol,
in particular (+)-tramadol.

For the active compound combination, it is particularly preferable if the compound A in group b) is chosen from:
codeine
dextropropxyphene
dihydrocodeine
diphenoxylate
ethylmorphine
meptazinol
nalbuphine
pethidine (meperidine)
tilidine
viminol
butorphanol
dezocine
nalorphine
pentazocine
buprenorphine
preferably
codeine
dextropropxyphene
dihydrocodeine
meptazinol
nalbuphine
tilidine
buprenorphine For the active compound combination, it is particularly preferable if the compound A in group c) is chosen from compounds according to formula I for which:
X is chosen from
OH, F, Cl, $OC(O)CH_3$ or H, preferably OH, F, OC(O)$CH_3$ or H,
and/or
$R^1$ is chosen from
$C_{1-4}$-alkyl, saturated and unsubstituted, branched or unbranched; preferably $CH_3$, $C_2H_5$, $C_4H_9$ or t-butyl, in particular $CH_3$ or $C_2H_5$, and/or R² and R³ independently of one another are chosen from
H, $C_{1-4}$-alkyl, saturated and unsubstituted, branched or unbranched; preferably H, $CH_3$, $C_2H_5$, i-propyl or t-butyl, in particular H or $CH_3$, preferably R³=H, or R² and R³ together form a $C_{5-6}$-cycloalkyl radical, saturated or unsaturated, unsubstituted or mono- or polysubstituted, preferably saturated and unsubstituted, in particular cyclohexyl.

and/or $R^9$ to $R^{13}$, where 3 or 4 of the radicals $R^9$ to $R^{13}$ must correspond to H, independently of one another are chosen from
H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched; preferably H, Cl, F, OH, $CF_2H$, $CF_3$, $OCH_3$ or $SCH_3$ or $R^{12}$ and $R^{11}$ form a 3,4-OCH=CH ring in particular
if $R^9$, $R^{11}$ and $R^{13}$ correspond to H, one of $R^{10}$ or $R^{12}$ also corresponds to H while the other is chosen from:
Cl, F, OH, $CF_2H$, $CF_3$, $OR^{14}$ or $SR^{14}$, preferably OH, $CF_2H$, $OCH_3$ or $SCH_3$ or if $R^9$ and $R^{13}$ correspond to H and $R^{11}$ corresponds to OH, $OCH_3$, Cl or F, preferably Cl, one of $R^{10}$ or $R^{12}$ also corresponds to H while the other corresponds to OH, $OCH_3$, Cl or F, preferably Cl, or if $R^9$, $R^{10}$, $R^{12}$ and $R^{13}$ correspond to H, $R^{11}$ is chosen from $CF_3$, $CF_2H$, Cl or F, preferably F, or if $R^{10}$, $R^{11}$ and $R^{12}$ correspond to H, one of $R^9$ or $R^{13}$ also corresponds to H while the other is chosen from OH, $OC_2H_5$ or $OC_3H_7$.

In this context, it is particularly preferable for compounds of group c) if the compounds of the formula I where R³=H are in the form of the diastereomers with the relative configuration Ia

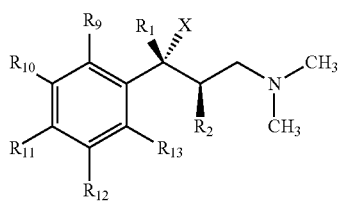

in particular in mixtures with a higher content of this diastereomer compared with the other diastereomer or as the isolated diastereomer and/or the compounds of the formula I are in the form of the (+)-enantiomer, in particular in mixtures with a higher content of the (+)-enantiomer compared with the (−)-enantiomer of a racemic compound or as the isolated (+)-enantiomer.

In this context, it is particularly preferable if compound A is chosen from the following group:
(2RS,3RS)-1-dimethylamino-3-(3-methoxy-phenyl)-2-methyl-pentan-3-ol
(2R,3R)-1-dimethylamino-3-(3-methoxy-phenyl)-2-methyl-pentan-3-ol,
(+)-(2R,3R)-1-dimethylamino-3-(3-methoxy-phenyl)-2-methyl-pentan-3-ol,
(2RS,3RS)-3-(3,4-dichlorophenyl)-1-dimethylamino-2-methyl-pentan-3-ol,
(2RS,3RS)-3-(3-difluoromethyl-phenyl)-1-dimethylamino-2-methyl-pentan-3-ol,
(2RS,3RS)-1-dimethylamino-2-methyl-3-(3-methylsulfanyl-phenyl)-pentan-3-ol,
(3RS)-1-dimethylamino-3-(3-methoxy-phenyl)-4,4-dimethyl-pentan-3-ol,
(2RS,3RS)-3-(3-dimethylamino-1-ethyl-1-hydroxy-2-methyl-propyl)-phenol,
(1RS,2RS)-3-(3-dimethylamino-1-hydroxy-1,2-dimethyl-propyl)-phenol,
(+)-(1R,2R)-3-(3-dimethylamino-1-hydroxy-1,2-dimethyl-propyl)-phenol,
(+)-(1R,2R)-3-(3-dimethylamino-1-hydroxy-1,2-dimethyl-propyl)-phenol,
(1R,2R)-3-(3-dimethylamino-1-ethyl-2-methyl-propyl)-phenol,
(−)-(1R,2R)-3-(3-dimethylamino-1-ethyl-2-methyl-propyl)-phenol,
(1S,2S)-3-(3-dimethylamino-1-ethyl-2-methyl-propyl)-phenol,
(+)-(1S,2S)-3-(3-dimethylamino-1-ethyl-2-methyl-propyl)-phenol,
(+)-(1R,2R)-acetic acid 3-dimethylamino-1-ethyl-1-(3-methoxy-phenyl)-2-methyl-propyl ester,
(1RS)-1-(1-dimethylaminomethyl-cyclohexyl)-1-(3-methoxy-phenyl)-propan-1-ol,
(2RS,3RS)-3-(4-chlorophenyl)-1-dimethylamino-2-methyl-pentan-3-ol,
(+)-(2R,3R)-3-(3-dimethylamino-1-ethyl-1-hydroxy-2-methyl-propyl)-phenol,
(2RS,3RS)-4-dimethylamino-2-(3-methoxy-phenyl)-3-methyl-butan-2-ol and
(+)-(2R,3R)-4-dimethylamino-2-(3-methoxy-phenyl)-3-methyl-butan-2-ol,
preferably as the hydrochloride.

For the active compound combination, it is particularly preferable if the compound A in group d) is chosen from compounds according to formula II for which:

X is chosen from
OH, F, Cl, $OC(O)CH_3$ or H, preferably OH, F or H, in particular OH, and/or R¹ is chosen from
$C_{1-4}$-alkyl, $CF_3$, OH, O—$C_{1-4}$-alkyl, Cl or F, preferably OH, $CF_3$ or $CH_3$, and/or $R^9$ to $R^{13}$, where 3 or 4 of the radicals $R^9$ to $R^{13}$ must correspond to H, independently of one another are chosen from
H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched; preferably H, Cl, F, OH, $CF_2H$, $CF_3$, $OCH_3$ or $SCH_3$ or $R^{12}$ and $R^{11}$ form a 3,4-OCH=CH ring in particular
if $R^9$, $R^{11}$ and $R^{13}$ correspond to H, one of $R^{10}$ or $R^{12}$ also corresponds to H while the other is chosen from:
Cl, F, OH, $CF_2H$, $CF_3$, $OR^{14}$ or $SR^{14}$, preferably OH, $CF_2H$, $OR^{14}$ or $SCH_3$, in particular OH or $OC_{1-3}$-alkyl, preferably OH or $OCH_3$, or if $R^9$ and $R^{13}$ correspond to H and $R^{11}$ corresponds to OH, $OCH_3$, Cl or F, preferably Cl, one of $R^{10}$ or $R^{12}$ also corresponds to H while the other corresponds to OH, $OCH_3$, Cl or F, preferably Cl, or
if $R^9$, $R^{10}$, $R^{12}$ and $R^{13}$ correspond to H, $R^{11}$ is chosen from $CF_3$, $CF_2H$, Cl or F, preferably F,
or
if $R^{10}$, $R^{11}$ and $R^{12}$ correspond to H, one of $R^9$ or $R^{13}$ also corresponds to H while the other is chosen from OH, $OC_2H_5$ or $OC_3H_7$.
very particularly preferably
if $R^9$, $R^{11}$ and $R^{13}$ correspond to H, one of $R^{10}$ or $R^{12}$ also corresponds to H while the other is chosen from:
Cl, F, OH, SH, $CF_2H$, $CF_3$, $OR^{14}$ or $SR^{14}$, preferably OH or $OR^{14}$, in particular OH or $OC_{1-3}$-alkyl, preferably OH or $OCH_3$.

In this context, it is particularly preferable for compounds of group d) if the compounds of the formula II are in the form of the diastereomers with the relative configuration IIa

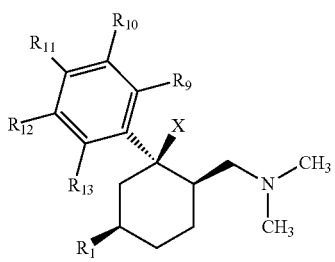

IIa in particular in mixtures with a higher content of this diastereomer compared with the other diastereomer or as the isolated diastereomer, and/or
the compounds of the formula II are in the form of the (+)-enantiomer, in particular in mixtures with a higher content of the (+)-enantiomer compared with the (−)-enantiomer of a racemic compound or as the isolated (+)-enantiomer.

In this context, it is particularly preferable if compound A is chosen from the following group:
(1RS, 3RS, 6RS)-6-dimethylaminomethyl-1-(3-methoxy-phenyl)-cyclohexane—1,3-diol,
(+)-(1R,3R,6R)-6-dimethylaminomethyl-1-(3-methoxy-phenyl)-cyclohexane-1,3-diol,
(1RS, 3RS,6RS)-6-dimethylaminomethyl-1-(3-hydroxy-phenyl)-cyclohexane-1,3-diol,
(1RS, 3SR, 6RS)-6-dimethylaminomethyl-1-(3-methoxy-phenyl)-cyclohexane-1,3-diol,
(+)-(1R,2R,5S)-3-(2-dimethylaminomethyl-1-hydroxy-5-methyl-cyclohexyl)-phenol or
(1RS, 2RS, 5RS)-3-(2-dimethylaminomethyl-1-hydroxy-5-trifluoromethyl-cyclohexyl)-phenol,
preferably as the hydrochloride.

For the active compound combination, it is particularly preferable if the compound A in group e) is chosen from compounds according to formula III for which:
X is chosen from
OH, F, Cl, $OC(O)CH_3$ or H, preferably OH, F or H, in particular F or H,
and/or
$R^9$ to $R^{13}$, where 3 or 4 of the radicals $R^9$ to $R^{13}$ must correspond to H, independently of one another are chosen from
H, Cl, F, OH, $CF_2H$, $CF_3$ or $C_{1-4}$-alkyl, saturated and unsubstituted, branched or unbranched; $OR^{14}$ or $SR^{14}$, where $R^{14}$ is chosen from $C_{1-3}$-alkyl, saturated and unsubstituted, branched or unbranched;
preferably H, Cl, F, OH, $CF_2H$, $CF_3$, $OCH_3$ or $SCH_3$ or $R^{12}$ and $R^{11}$ form a 3,4-OCH=CH ring in particular characterized in that
if $R^9$, $R^{11}$ and $R^{13}$ correspond to H, one of $R^{10}$ or $R^{12}$ also corresponds to H while the other is chosen from:
Cl, F, OH, $CF_2H$, $CF_3$, $OR^{14}$ or $SR^{14}$, preferably OH, $CF_2H$, $OR^{14}$ or $SCH_3$, in particular OH or $OC_{1-3}$-alkyl, preferably OH or $OCH_3$,
or
if $R^9$ and $R^{13}$ correspond to H and $R^{11}$ corresponds to OH, $OCH_3$, Cl or F, preferably Cl, one of $R^{10}$ or $R^{12}$ also corresponds to H while the other corresponds to OH, $OCH_3$, Cl or F, preferably Cl,
or
if $R^9$, $R^{10}$, $R^{12}$ and $R^{13}$ correspond to H, $R^{11}$ is chosen from $CF_3$, $CF_2H$, Cl or F, preferably F,
or
if $R^{10}$, $R^{11}$ and $R^{12}$ correspond to H, one of $R^9$ or $R^{13}$ also corresponds to H while the other is chosen from OH, $OC_2H_5$ or $OC_3H_7$,
very particularly preferably
if $R^9$, $R^{11}$ and $R^{13}$ correspond to H, one of $R^{10}$ or $R^{12}$ also corresponds to H while the other is chosen from:
Cl, F, OH, SH, $CF_2H$, $CF_3$, $OR^{14}$ or $SR^{14}$, preferably OH or $OR^{14}$, in particular OH or $OC_{1-3}$-alkyl, preferably OH or $OCH_3$.

In this context, it is particularly preferable for compounds of group e) if the compounds of the formula III are in the form of their diastereomers with the relative configuration IIIa

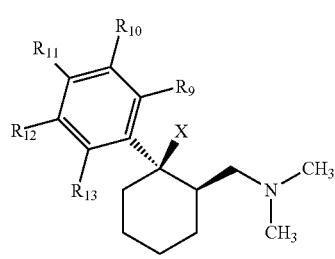

IIIa in particular in mixtures with a higher content of this diastereomer compared with the other diastereomer or as the isolated diastereomer and/or
the compounds of the formula III are in the form of the (+)-enantiomer, in particular in mixtures with a higher content of the (+)-enantiomer compared with the (−)-enantiomer of a racemic compound or as the isolated (+)-enantiomer.

In this context, it is particularly preferable if compound A is chosen from the following group:
(+)-(1R,2R)-3-(2-dimethylaminomethyl-1-fluoro-cyclohexyl)-phenol,
(+)-(1S,2S)-3-(2-dimethylaminomethyl-cyclohexyl)-phenol or
(1S,2S)-3-(2-dimethylaminomethyl-cyclohexyl)-phenol
or
(−)-(1R,2R)-3-(2-dimethylaminomethyl-cyclohexyl)-phenol,
(1R,2R)-3-(2-dimethylaminomethyl-cyclohexyl)-phenol,
(−)-(1R,2R)-[2-(3-methoxy-phenyl)-cyclohexylmethyl]-dimethylamine,
(1R,2R)-[2-(3-methoxy-phenyl)-cyclohexylmethyl]-dimethylamine,
preferably as the hydrochloride.

In a generally particularly preferred form of the active compound combination according to the invention the compound B is chosen from:
darifenacin, duloxetine, oxybutinin or tolterodine,
preferably is chosen from duloxetine, oxybutinin or tolterodine,
preferably is chosen from
oxybutinin or tolterodine.

The invention also provides a medicament, preferably for treatment of an increased urge to urinate or urinary incontinence, comprising an active compound combination according to the invention and optionally suitable additives and/or auxiliary substances.

Suitable additives and/or auxiliary substances in the context of this invention are all the substances known to the expert from the prior art for achieving pharmaceutical formulations. The choice of these auxiliary substances and the amounts thereof to be employed depend on whether the medicament is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration of the skin, are examples of suitable forms for percutaneous administration. Examples of auxiliary substances and additives for the oral administration forms are disintegrating agents, lubricants, binders, fillers, mold release agents, with appropriate solvents, flavorings, sugar, in particular carrier agents, diluents, dyestuffs, antioxidants, etc. Waxes and fatty acid esters, inter alia, can be used for suppositories and carrier substances, preservatives, suspension auxiliaries etc. can be used for compositions for parenteral administration. The amounts of active compound to be administered to patients vary as a function of the weight of the patient, the mode of administration and the severity of the disease. The compounds according to the invention can be released in a delayed manner from formulation forms for oral, rectal or percutaneous use. In the indication according to the invention, appropriate sustained release formulations, in particular in the form of a "once-daily" preparation which has to be taken only once a day, are particularly preferred.

Medicaments which comprise at least 0.05 to 90.0% of the active compound, in particular dosages with a low action, in order to avoid side effects or analgesic actions, are furthermore preferred. 0.1 to 5,000 mg/kg, in particular 1 to 500 mg/kg, preferably 2 to 250 mg/kg of body weight of at least one compound of the formula I are conventionally administered. However, administration of 0.01-5 mg/kg, preferably 0.03 to 2 mg/kg, in particular 0.05 to 1 mg/kg of body weight, is also likewise preferred and conventional.

Auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatins, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic rubbers, gum acacia, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The medicaments and pharmaceutical compositions according to the invention are prepared with the aid of agents, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus, e.g., for a solid formulation, such as a tablet, the active compound of the medicament can be granulated with a pharmaceutical carrier, e.g., conventional tablet constituents, such as maize starch, lactose, sucrose, sorbitol, talc, magnesium stearate, dicalcium phosphate or pharmaceutically acceptable gums, and pharmaceutical diluents, such as, e.g., water, in order to form a solid composition which comprises the active compound in homogeneous distribution. Homogeneous distribution is understood here as meaning that the active compound is distributed uniformly over the entire composition, so that this can be easily divided into unit dose forms, such as tablets, pills or capsules, with the same action. The solid composition is then divided into unit dose forms. The tablets or pills of the medicament according to the invention or of the compositions according to the invention can also be coated, or compounded in another manner, in order to provide a dose form with delayed release. Suitable coating compositions are, inter alia, polymeric acids and mixtures of polymeric acids with materials such as, e.g., shellac, cetyl alcohol and/or cellulose acetate.

Although the medicaments according to the invention show only a low degree of side effects, it may be of advantage, for example to avoid certain forms of dependency, also to use morphine antagonists, in particular naloxone, naltrexone and/or levallorphan, in addition to the combination of compounds A and B.

The invention also relates to a method for treatment of an increased urge to urinate or urinary incontinence, in which the active compound combination of compound A and compound B, in particular in a therapeutically active (in each case) dosage, is used.

The following examples are intended to explain the invention without the subject matter of the invention being limited thereto.

EXAMPLES

Example 1

Test System of Cystometry on Anaesthetized Naïve Rats

The cystometric investigation on naive female rats was carried out by the method of Kimura et al. (Kimura et al., 1996, Int. J. Urol. 3:218-227). The abdomen of anaesthetized, ventilated rats is opened up and the ureter is ligated. The urine is drained from the kidneys. A catheter is inserted into the bladder and fixed. Saline is infused into the bladder via this by means of an infusion pump, until the bladder shows rhythmic spontaneous activity in the form of contractions which can be recorded via a connected pressure transducer. After stable starting values are reached, the test substance is administered intravenously. An influence on bladder function manifests itself via suppression of the spontaneous contractions.

In the present example, compound A ((+)-(2R,3R)-1-dimethylamino-3-(3-methoxy-phenyl)-2-methyl-pentan-3-ol; hydrochloride) in the dosage of 0.1 mg/kg intravenous was combined with compound B (oxybutynin) in the dosage of 0.03 mg/kg intravenous and the action of this combination was compared with that of the individual substances. The individual substances and combination showed an inhibition of the rate of contractions (micturition events/min). The data are summarized in the following table.

| Substance | Compound A 0.1 mg/kg i.v. | Compound B 0.03 mg/kg i.v | Compound A 0.1 mg/kg i.v. + compound B 0.3 mg/kg i.v. | Vehicle control i.v. |
|---|---|---|---|---|
| Inhibition of the rate of contractions compared with the pretest [% MPE] | 21.7% | 10.7% | 42.5% | 4.0% |

A suppression of spontaneous contractions in the rats was measurable with all the substances and combinations listed here.

The combination of substances which was investigated shows a positive action on bladder regulation and is thus suitable for treatment of urinary incontinence.

Example 2

Parenteral Administration Form 20 g tramadol and 1 g tolterodine is dissolved in 1 l of water for injection purposes at room temperature and the solution is then adjusted to isotonic conditions by addition of NaCl.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A composition of matter comprising as an admixture (+)-(2R,3R)-1-dimethylamino-3-(3-methoxy-phenyl)-2-methyl-pentan-3-ol or a salt thereof with a physiologically tolerated acid and oxybutynin or a salt thereof with a physiologically tolerated acid at dosages that provide a synergistic effect for the treatment of urinary incontinence.

2. The composition of matter of claim 1, wherein one or more of (+)-(2R,3R)-1-dimethylamino-3-(3-methoxy-phenyl)-2-methyl-pentan-3-ol and oxybutynin is present in the form of a free base.

3. The composition of matter of claim 1, wherein oxybutynin is present in the form of an isolated enantiomer.

4. The composition of matter of claim 1, wherein oxybutynin is present in the form of a mixture of stereoisomers.

5. The composition of matter of claim 4, wherein oxybutynin is present in the form of a racemic mixture.

6. The composition of matter of claim 1, wherein (+)-(2R,3R)-1-dimethylamino-3-(3-methoxy-phenyl)-2-methyl-pentan-3-ol is in the form of a hydrochloride salt.

7. A pharmaceutical formulation comprising as an active compound combination a composition of matter according to claim 1 and at least one pharmaceutically suitable additive or auxiliary substance.

* * * * *